United States Patent [19]
Flavin et al.

[11] Patent Number: 5,504,111
[45] Date of Patent: Apr. 2, 1996

[54] USE OF 2,3 ALKYLCARBONYLOXYBENZOIC ACID IN TREATING ADULT RESPIRATORY DISTRESS SYNDROME

[75] Inventors: Michael T. Flavin, Darien; Deanna J. Nelson, Libertyville, both of Ill.; Julian F. Borgia deceased, by Lee Ann Borgia, legal representative, late of Bellmead, N.J.; Gary Jesmok, Madison, Conn.

[73] Assignee: Medichem Research, Inc., Lemont, Ill.

[21] Appl. No.: 366,885

[22] Filed: Dec. 30, 1994

[51] Int. Cl.$^6$ .................................................. A61K 31/215
[52] U.S. Cl. ..................... 514/530; 514/568; 514/531; 514/532; 514/533; 514/543; 514/544; 514/546; 514/547; 514/548; 514/552
[58] Field of Search ..................... 514/568, 530, 514/531, 532, 533, 543, 544, 546, 547, 548, 552

[56] References Cited

U.S. PATENT DOCUMENTS

| | | | |
|---|---|---|---|
| 4,443,476 | 4/1984 | Lomen | 424/317 |
| 4,447,451 | 5/1984 | Mueller | 424/317 |
| 4,686,100 | 8/1987 | Raffin et al. | 424/85 |
| 4,703,040 | 10/1987 | Markov | 514/23 |
| 5,198,420 | 3/1993 | Donahoe et al. | 424/85.8 |
| 5,338,727 | 8/1994 | Glass et al. | 514/19 |
| 5,389,522 | 2/1995 | Repine et al. | 435/7.4 |
| 5,418,219 | 5/1995 | Ueda | 514/12 |

*Primary Examiner*—Marianne M. Cintins
*Assistant Examiner*—Keith MacMillan
*Attorney, Agent, or Firm*—Banner & Allegretti, Ltd.

[57] ABSTRACT

This invention relates to methods for treating Adult Respiratory Distress Syndrome (ARDS) which involves the administration of 2,3-alkylcarbonyloxybenzoic acid and salts thereof wherein the alkyl group has 2–18 carbon atoms.

2 Claims, 3 Drawing Sheets

USE OF 2,3 ALKYLCARBONYLOXYBENZOIC ACID IN TREATING ADULT RESPIRATORY DISTRESS SYNDROME

FIELD OF THE INVENTION

This invention is in the field of treating diseases originating from oxidative processes.

BACKGROUND OF THE INVENTION

The inflammatory response is one of the most important physiological mechanisms for the maintenance of human health. However, disorders of inflammation or an inappropriate inflammatory response can result in tissue injury, morbidity or mortality.

The cascade of biochemical processes that initiate and regulate the inflammatory response opens a variety of approaches for therapeutic intervention. However, the complexity of cellular events and physiological processes involved in acute inflammation preclude the use of a single pharmacological agent to achieve total therapeutic effectiveness.

At the cellular level the oxidative products of arachidonic acid metabolism can be thought of as members of a family of chemical substances produced in the body as part of the immunochemical response. These agents constitute a method for protection by which viruses, bacteria, or certain cells such as tumor or damaged cells are recognized and destroyed.

Upon release from cellular phospholipids, arachidonic acid is oxidatively metabolized by two principal systems, the cyclooxgenase and the 5-lipoxygenase pathways. Metabolism via the cyclooxygenase pathway sequentially generates prostaglandin endoperoxides and the corresponding endoperoxide alcohols. The biological effects of prostaglandin endoperoxides include smooth muscle contraction, complex cardiovascular effects, and rapid and irreversible platelet aggregation.

Arachidonic acid metabolism via the 5-lipoxygenase pathway produces the unstable intermediate, 5-(S)-hydroperoxy-7,9,11,14-[E,Z,Z,Z]eicosatetraenoic acid [5-(S)-HPETE]. This species may be reduced to the 5-(S)-hydroxy derivative or converted to the unstable allylic epoxide leukotriene $A_4$ ($LTA_4$). $LTA_4$ can be converted to the potent chemotactic agent $LTB_4$ or to the first of a series of peptidoleukotrienes, $LTC_4$. The peptidoleukotrienes $LTC_4$, $LTD_4$ and $LTE_4$ comprise the compounds that have been termed the "slow reacting substance of anaphylaxis" and are potent broncho-constrictors and pulmonary vasoconstrictors.

Formation and release of these arachidonic acid metabolites both inter- and extracellularly mark the mobilization of bodily defenses. Further evidence of this mobilization is seen in the clinical symptoms characteristic of systemic inflammatory reaction. These include a pronounced increase in mean pulmonary artery pressure and a decrease in arterial $PO_2$. Cardiac output and stroke volume decline while systemic vascular resistance increases. Heart rate exhibits a biphasic pattern, with an initial increase followed by a return to baseline and a subsequent elevation. Oxygen consumption increases significantly. Coincident with these cardiopulmonary events, the arterial neutrophil count declines precipitously as a consequence of pulmonary sequestration of these inflammatory cells. The release of oxygen radicals (toxic oxygen species) and proteolytic enzymes that follows this sequestration results in tissue injury marked by increased microvascular permeability to solutes and protein.

With the possible exception of clucocorticoids, there are no therapeutic agents known to be effective in preventing or ameliorating the tissue injury, such as microvascular damage, associated with acute inflammation that occurs during the early development of Adult Respiratory Distress Syndrome (ARDS). It has been discovered that attenuation of damaging components of inflammation will diminish the morbidity or mortality associated with a variety of human diseases where inflammatory processes are responsible for tissue injury.

SUMMARY OF THE INVENTION

This invention encompasses methods for treating diseases originating from oxidative processes. In particular, the invention involves a method for treating Adult Respiratory Distress Syndrome (ARDS) comprising administering to a person in need of ARDS treatment an effective therapeutic amount of 2,3alkylcarbonyloxybenzoic acid wherein the alkylcarbonyloxy group has 2–18 carbon atoms. The alkyl moieties may be the same or different and may be branched or straight chain alkyl groups. The alkyl group may have ring structures with 3 to 7 member rings; and may contain one or more alkene or alkyne groups. The alkyl moiety may contain ether or thioether linkages.

An important use of the present invention should be in therapeutic treatment and/or prevention of sepsis and septic shock. Many of the physiological and, indeed, the pathological processes involved with ARDS have also been demonstrated to be involved in the condition of sepsis and septic shock. The present invention acts to block and/or modulate these disease processes and lead to prevention or therapy of sepsis and septic shock.

DETAILED DESCRIPTION OF THE INVENTION

Figure 1:
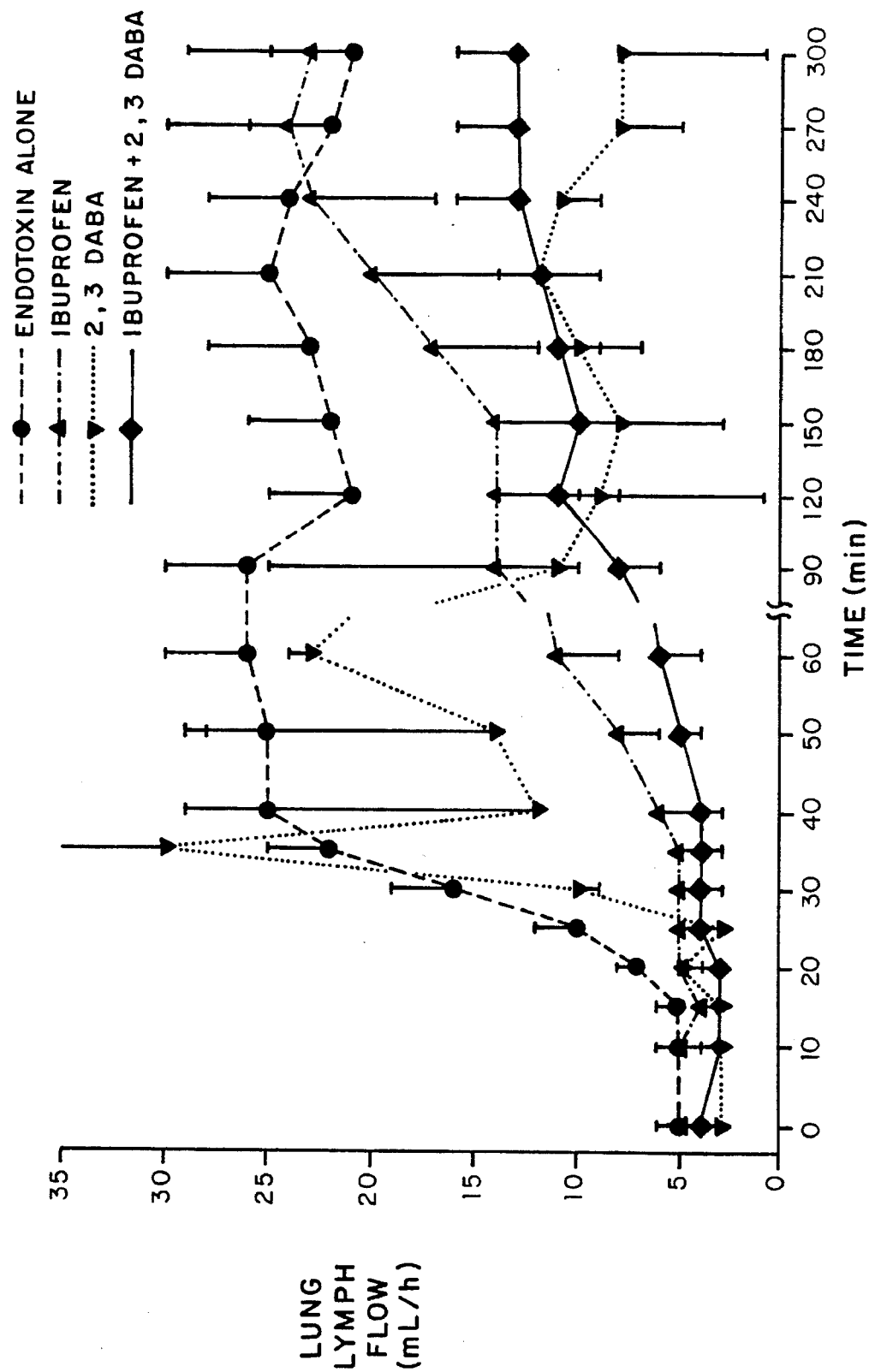
FIG. 1 shows the effect of ibuprofen and 2,3-diacetoxybenzoic acid on lung lymph flow vs time with endotoxin.

Clinically, inflammatory disease such as ARDS is manifested by an increased microvascular permeability to protein and solutes resulting in pulmonary edema. Tate, R. M. and Repine, J.: Neutrophils and Adult Respiratory Distress Syndrome. Am. Rev. Respir. Dis. 128: 552–559, 1983. Gram-negative sepsis is the most common setting in which ARDS develops. Newman, J. H.: Sepsis and Pulmonary Edema. Clin. Chest Med. 6: 371–391, 1985. The liposaccharide components of gram-negative bacteria (endotoxin) are thought to be responsible for initiating the inflammatory processes which result in lung injury manifested by increases in lung microvascular permeability. The pathology of this process (lung injury) has been most thoroughly studied in the conscious sheep with lung-lymph fistula. Brigham, J., Begley, C., and Bernard, G.: Septicemia and Lung Injury, Clin. Lab. Med. 3: 719–744, 1983.

Endotoxin infusion in sheep produces alterations in lung microvascular permeability, as assessed by increases in lung lymph flow and lung lymph protein clearance (Brigham, K., Harris, T. R., Bowers, R. E., Roselli, R. J.: Lung Vascular Permeability Inferences From Measures of Plasma to Lung Lymph Protein Transport. Lymphology 12:177–190 (1979)), which are analogous to those seen clinically in the early diagnosis of ARDS. Because the inflammatory insult (endotoxin) is similar to that producing ARDS in humans and the pathophysiologic features in the two situations are similar, the sheep preparation appears to be a reasonable animal model of the clinical situation. Using the sheep lung-lymph fistula preparation, we have shown that the combination therapy of ibuprofen and 2,3-diacetoxybenzoic acid significantly reduces the increase in lung microvascular permeability observed following gram-negative endotoxin infusion (see FIGS. 1, 2, 3).

Ibuprofen, a non-steroidal anti-inflammatory agent, is known to intervene in the cyclooxgenase pathway and to block the biosynthesis of certain prostaglandins, which act as mediators of inflammation.

Ibuprofen has been shown to ameliorate a number of the pathologic cardiopulmonary manifestations of endotoxin-induced intravascular inflammation without affecting the microvascular injury component of the response. Adams, T. and Traber, D. L.: The Effect of a Prostaglandin Synthetase Inhibitor, Ibuprofen, on the Cardiopulmonary Response to Endotoxin in Sheep. Circulatory Shock 9: 481–489, 1982. Snapper, J., Hutchinson, A., Ogletree, M. L., and Brigham, K. L.: Effect of Cyclooxygenase Inhibitors on Alterations in Lung Mechanics Caused by Endotoxemia in the Unanesthetized Sheep. J. Clin. Invest. 72: 63–76, 1983. The pharmacological capability to diminish the inflammation associated with pulmonary microvascular injury comprises the focus of the present invention.

Lung lymph fistulae were surgically prepared in sheep according to the method of Staub et al. (Staub, N. C., Bland, R. D., Brigham, K. L., Demling, R. H. and Erdman, A. J.: Preparation of Chronic Lung Lymph Fistulas in Sheep. J. Surg. Res. 19:315–320 (1975)) in order to assess lung microvascular permeability changes. Briefly, under halothane anesthesia, the efferent duct of the caudal mediastinal lymph node was cannulated through a right thoracotomy with a silastic catheter. The distal end of the node was ligated at the inferior pulmonary ligament, and any visible diaphragmatic lymphatic vessels entering the node proximal to the ligation were cauterized to eliminate systemic lymph contamination. The silastic catheter was externalize onto the chest following wound closure, and the animal was allowed a one-week recovery period.

In the sheep model described above, administration of ibuprofen significantly inhibited the increase in pulmonary pressure observed during the "first phase" of endotoxin-induced inflammation. However, microvascular injury, as evidence by increased lung lymph flow and protein transport, was not moderated.

Endotoxin infusion in conscious sheep produces alternations in lung microvascular permeability, as assessed by increases in lung lymph flow and lung lymph protein clearance (Brigham, K., Harris, T. R., Bowers, R. E., Roselli, R. J.: Lung Vascular Permeability Inferences From Measures of Plasma to Lung Lymph Protein Transport. Lymphology 12:177–190 (1979)) which are analogous to those seen clinically in the early diagnosis of ARDS. Using the sheep lung-lymph fistula preparation, we have shown that the combination of ibuprofen and 2,3diacetoxybenzoic acid significantly reduces the increase in lung microvascular permeability observed following gram-negative endotoxin infusion (see FIGS. 1 and 2).

The use of only 2,3-diacetoxybenzoic acid resulted in no moderation of the "first phase" manifestations of inflammation, but significant decreases in both sheep lymph flow (see FIG. 1) and lung lymph protein clearance (see FIG. 2) were observed.

We have found that combinations of ibuprofen and 2,3-diacetoxybenzoic acid, when administered to sheep, are unexpectedly and significantly effective in decreasing the endotoxin-induced inflammatory response. In addition to moderation of the "first phase" manifestations of inflammation, significant decreases in both sheep lung lymph flow (microvascular injury) (see FIG. 1) and lung lymph protein clearance (see FIG. 2) were observed. In addition, FIG. 3 shows the effect of lowering $P_{PA}$. This effect was sustained for several hours.

For example, FIG. 1 shows the evaluation of the therapeutic efficacy of 2,3-diacetoxybenzoic acid in combination with ibuprofen in the ARDS sheep model. The pathology of endotoxin-treated group is assessed by an increase in lung lymph flow. The data are reported as mean ±SEM. Endotoxin (055:85 E. coli) treated group (1 ug/kg) over 10 minutes, N=8. Ibuprofen pre-treatment group, 20 mg/kg over 60 minutes, N=6. Ibuprofen+2,3-diacetoxybenzoic acid pre-treatment group, 150 mg/kg over 60 minutes, N=6.

Figure 2:
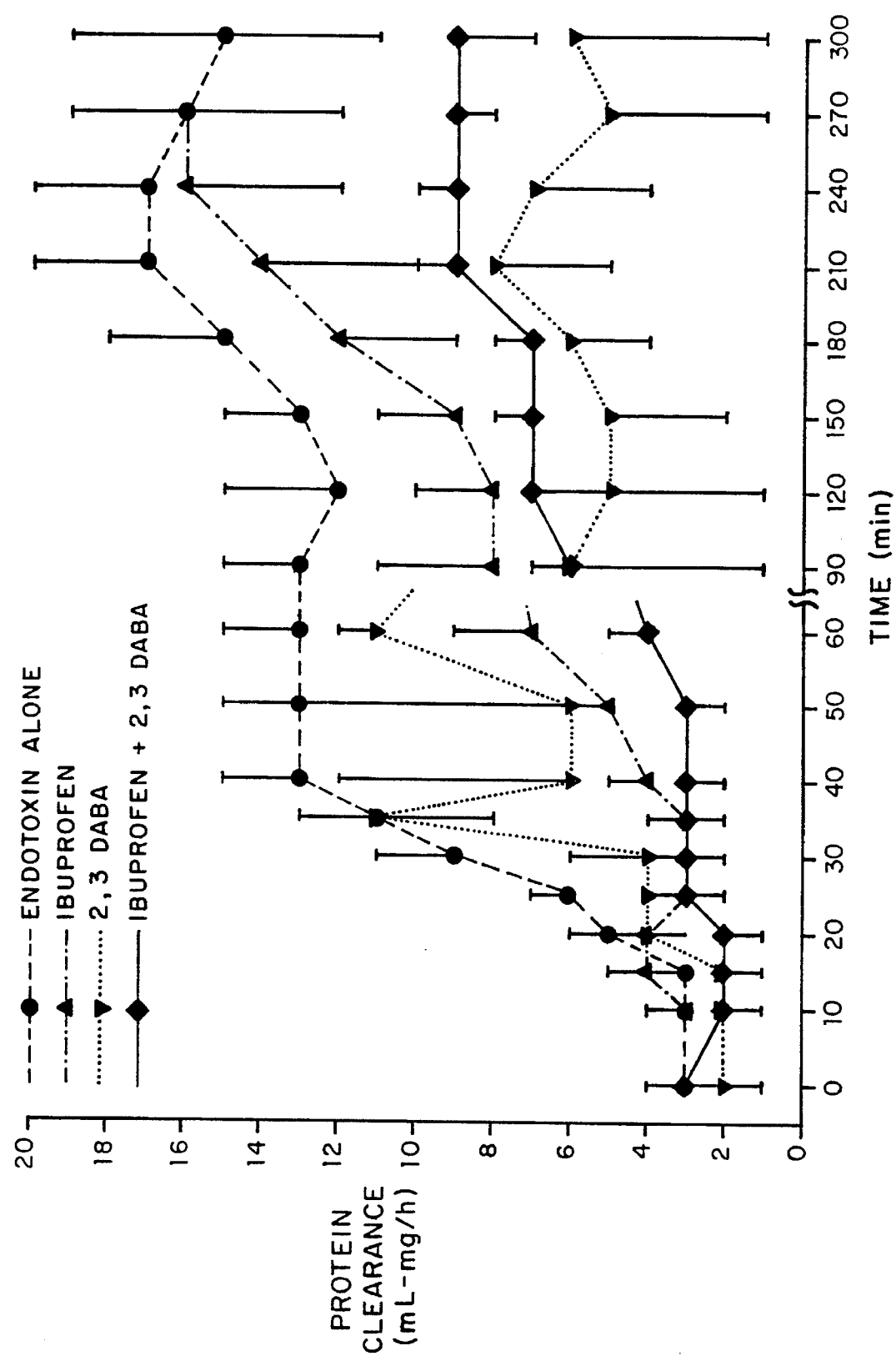
FIG. 2 shows the effect of ibuprofen and 2,3-diacetoxybenzoic acid on protein clearance vs time with endotoxin.
Figure 3:
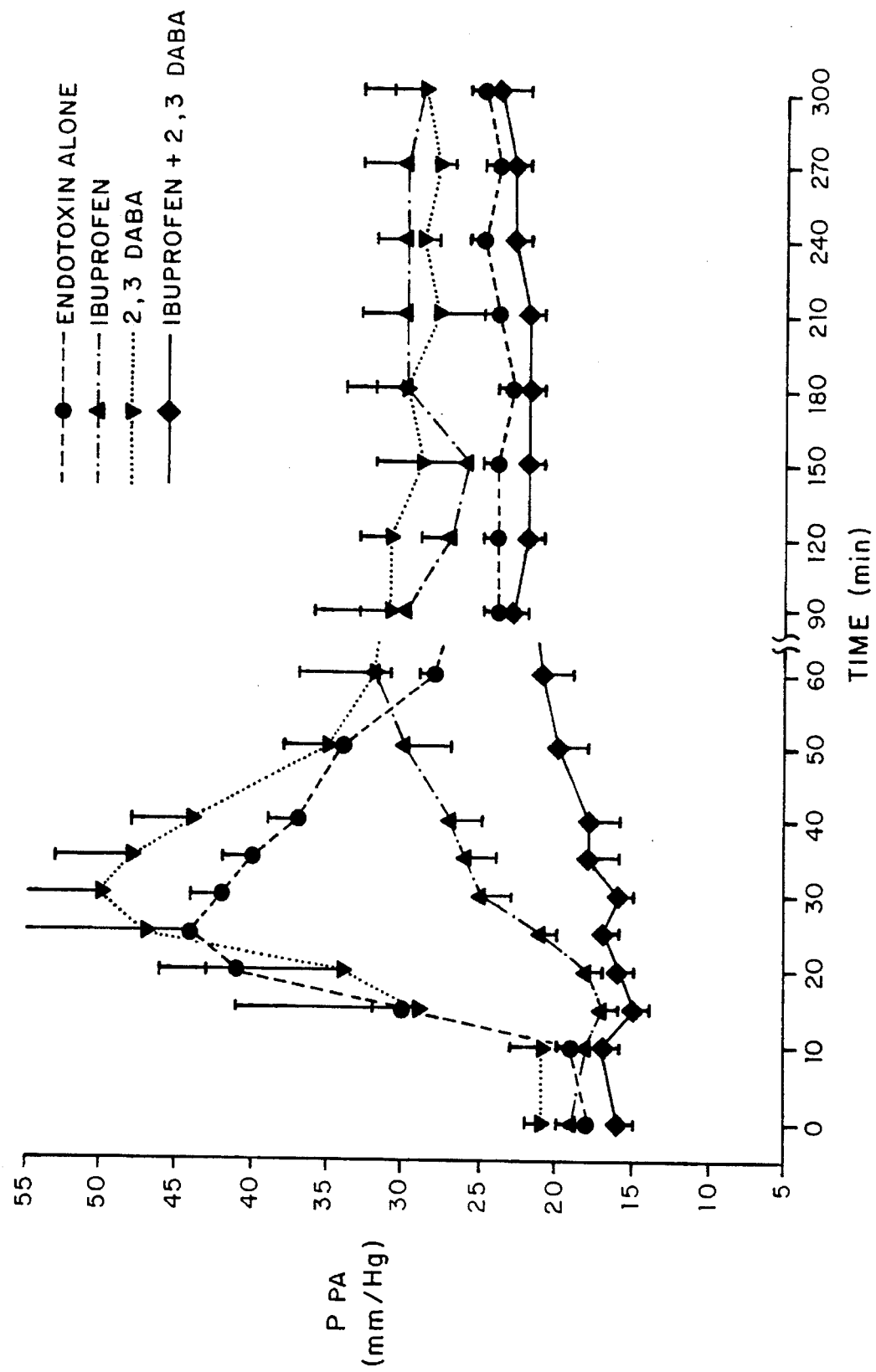
FIG. 3 shows the effect of ibuprofen and 2,3-diacetoxybenzoic acid on $P_{PA}$ VS time with endotoxin.

FIG. 2 shows the evaluation of the therapeutic efficacy of 2,3diacetoxybenzoic acid in combination with ibuprofen in the ARDS sheep model. The pathology of the endotoxin-treated group is assessed by an increase in lung lymph protein clearance. The data are reported as mean ±SEM. Endotoxin (055:85 E. coli) treated group (1 ug/kg) over 10 minutes, N=8. Ibuprofen pre-treatment group, 30 mg/kg over 60 minutes, N=6. Ibuprofen+2,3diacetoxybenzoic acid pre-treatment group, 150 mg/kg over 60 minutes, N=6.

ARDS may develop from a number of other inciting or predisposing conditions besides bacterial septicemia. Since the humoral and biochemical mechanisms leading to injury are believed to be similar, irrespective of the inciting factor, the combination therapy of ibuprofen and 2,3-diacetoxybenzoic acid may be effective in the prevention or treatment of ARDS secondary to trauma, drug overdose, aspiration, hyperoxia, toxins, massive blood transfusion, disseminated intravascular coagulation and pancreatitis, as well as other predisposing conditions.

Acute inflammation is also manifested in tissue reperfusion following ischemic myocardial injury and stroke in the systemic administration of recombinant interleukin-2, and in systemic administration of human recombinant tumor necrosis factor. The drug combinations described in this patent may be therapies for the acute inflammation associated with these clinical conditions.

The examples set out above are intended to illustrate the present invention and not to limit it in spirit or scope.

What is claimed is:

1. A method for treating Adult Respiratory Distress Syndrome (ARDS) comprising administering to a subject in need of ARDS therapy an effective therapeutic amount of 2,3-alkylcarbonyloxybenzoic acid and salts thereof wherein the alkylcarbonyl group has 2–18 carbon atoms.

2. The method of claim 1 wherein ibuprofen is administered in combination with the 2,3-alkylcarbonyloxybenzoic acid.

* * * * *

UNITED STATES PATENT AND TRADEMARK OFFICE
CERTIFICATE OF CORRECTION

PATENT NO.: 5,504,111

DATED: April 2, 1996

INVENTOR(S): Michael T. Flavin et al.

It is certified that error appears in the above-identified patent and that said Letters Patent is hereby corrected as shown below:

On the Title page, item [54], after "2,3" insert hyphen;

In Column 1, line 1, after "2,3" insert hyphen;

In Column 2, line 21, between "2,3" and "alkylcarbonyloxybenzoic" insert hyphen;

In Column 2, line 44, delete "VS" and insert --vs--;

In Column 3, line 64, between "2,3" and "diacetoxybenzoic" insert hyphen;

In Column 4, line 27, between "2,3" and "diacetoxybenzoic" insert hyphen; and

In Column 4, line 33, between "2,3" and "diacetoxybenzoic" insert hyphen.

Signed and Sealed this

Tenth Day of September, 1996

Attest:

BRUCE LEHMAN

*Attesting Officer*  *Commissioner of Patents and Trademarks*